United States Patent
Ridler et al.

(10) Patent No.: US 10,511,189 B2
(45) Date of Patent: Dec. 17, 2019

(54) IMPLANTABLE MEDICAL DEVICE CHARGING

(71) Applicant: Cochlear Limited, Macquarie University, NSW (AU)

(72) Inventors: Oliver John Ridler, Cherrybrook (AU); Kurt Forrester, Bangor (AU)

(73) Assignee: Cochlear Limited, Macquarie University, NSW (AU)

( * ) Notice: Subject to any disclaimer, the term of this patent is extended or adjusted under 35 U.S.C. 154(b) by 237 days.

(21) Appl. No.: 15/219,621

(22) Filed: Jul. 26, 2016

(65) Prior Publication Data

US 2017/0040841 A1 Feb. 9, 2017

Related U.S. Application Data

(60) Provisional application No. 62/200,157, filed on Aug. 3, 2015.

(51) Int. Cl.
| | |
|---|---|
| *H02J 7/00* | (2006.01) |
| *H02J 50/10* | (2016.01) |
| *H02J 7/02* | (2016.01) |
| *A61N 1/05* | (2006.01) |
| *A61N 1/378* | (2006.01) |

(52) U.S. Cl.
CPC ............ *H02J 50/10* (2016.02); *A61N 1/0541* (2013.01); *A61N 1/3787* (2013.01); *H02J 7/025* (2013.01)

(58) Field of Classification Search
CPC ........ H02J 50/10; H02J 7/04; A61N 1/36036; A61N 1/0541

USPC ........................................ 320/108; 307/104
See application file for complete search history.

(56) References Cited

U.S. PATENT DOCUMENTS

| | | | |
|---|---|---|---|
| 7,349,741 B2 | 3/2008 | Maltan et al. | |
| 8,155,746 B2 | 4/2012 | Maltan et al. | |
| 8,280,524 B2 | 10/2012 | Duftner et al. | |
| 8,811,643 B2 | 8/2014 | Crawford et al. | |
| 8,831,256 B2 | 9/2014 | Fort et al. | |
| 8,831,728 B2 | 9/2014 | Duftner et al. | |
| 8,914,127 B1 | 12/2014 | Yan et al. | |
| 2010/0013321 A1* | 1/2010 | Onishi | G08C 17/04 307/104 |
| 2010/0137948 A1* | 6/2010 | Aghassian | A61N 1/3787 607/61 |
| 2011/0112608 A1 | 5/2011 | Zierhofer | |
| 2012/0150259 A1 | 6/2012 | Meskens | |

(Continued)

FOREIGN PATENT DOCUMENTS

| | | |
|---|---|---|
| WO | 2010/081915 A2 | 7/2010 |
| WO | 2012/016587 A1 | 2/2012 |

*Primary Examiner* — Zixuan Zhou
(74) *Attorney, Agent, or Firm* — Edell, Shapiro & Finnan, LLC

(57) ABSTRACT

Embodiments presented herein are generally directed to inductive charging techniques in an implantable medical device system comprising an inductive charger and an external component. The external component includes a rechargeable battery and an inductive coil that is configured to form an inductive charging link with a charging coil in the inductive charger to receive power signals from the inductive charger. A voltage increasing converter in the external component is configured to step-up a voltage of the power signals received from the inductive charger for use in recharging the rechargeable battery.

20 Claims, 6 Drawing Sheets

(56) References Cited

U.S. PATENT DOCUMENTS

| | | | |
|---|---|---|---|
| 2013/0026981 A1* | 1/2013 | Van Der Lee | H02J 5/005 |
| | | | 320/108 |
| 2013/0182874 A1 | 7/2013 | Buehlmann | |
| 2014/0379047 A1 | 12/2014 | Meskens | |
| 2015/0005844 A1 | 1/2015 | Duftner et al. | |
| 2015/0028803 A1* | 1/2015 | Shevde | H02J 7/0052 |
| | | | 320/108 |
| 2015/0244341 A1* | 8/2015 | Ritter | H01F 38/14 |
| | | | 307/104 |
| 2015/0380972 A1 | 12/2015 | Fort | |
| 2016/0006292 A1* | 1/2016 | Hatanaka | H02J 17/00 |
| | | | 320/108 |

* cited by examiner

IMPLANTABLE MEDICAL DEVICE CHARGING

CROSS REFERENCE TO RELATED APPLICATIONS

This application claims priority to U.S. Provisional Application No. 62/200,157 entitled "Implantable Medical Device Charging," filed Aug. 3, 2015, the content of which is hereby incorporated by reference herein.

BACKGROUND

Field of the Invention

The present invention relates generally to implantable medical devices.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process. Many of these functional components utilize power and/or data received from external components that are part of, or operate in conjunction with, the implantable medical device.

SUMMARY

In one aspect an implantable medical device system is provided. The implantable medical device system comprises: an inductive charger including a charger coil; an external component including: a rechargeable battery, an inductive coil arrangement configured to form an inductive charging link with the charging coil to receive power signals from the inductive charger, and a voltage increasing converter configured to step-up a voltage of the power signals received from the inductive charger for use in charging the rechargeable battery.

In another aspect a method is provided. The method comprises: transmitting, via an external coil arrangement of an external component of a hearing prosthesis, at least one of power and data to an implantable component of the hearing prosthesis; receiving, via the external coil arrangement, voltage-limited power signals transmitted by a charging component over an inductive charging link; increasing/boosting, with a voltage increasing converter of the external component, the voltage of the voltage-limited power signals to generate voltage-increased charging signals; and delivering the voltage-increased charging signals to a rechargeable battery of the hearing prosthesis.

In another aspect an external component of an implantable medical device system is provided. The external component comprises: a rechargeable battery; a dual-function coil arrangement configured for transcutaneous communication with an implantable component of the implantable medical device system, wherein the dual-function coil arrangement is further configured to receive voltage-limited charging signals from a charging component; and a voltage increasing converter and a voltage decreasing converter connected in parallel between the dual-function coil arrangement and the rechargeable battery

BRIEF DESCRIPTION OF THE DRAWINGS

Embodiments of the present invention are described herein in conjunction with the accompanying drawings, in which.

DETAILED DESCRIPTION

Embodiments presented herein are generally directed to inductive charging techniques in an implantable medical device system comprising an inductive charger and an external component. The external component includes a rechargeable battery and an inductive coil that is configured to form an inductive charging link with a charging coil in the inductive charger to receive power signals from the inductive charger. A voltage increasing converter in the external component is configured to step-up a voltage of the power signals received from the inductive charger for use in charging the rechargeable battery.

Embodiments of the present invention are described herein primarily in connection with one type of implantable medical device system, namely partially implantable auditory or hearing systems comprising an external component and an internal (implantable) component. Implantable hearing systems include, but are not limited to, auditory brain stimulators, cochlear implants, bone conduction devices, and mechanical stimulators. It is to be appreciated that embodiments of the present invention may be implemented in any partially or fully implantable medical device system now known or later developed.

Figure 1:
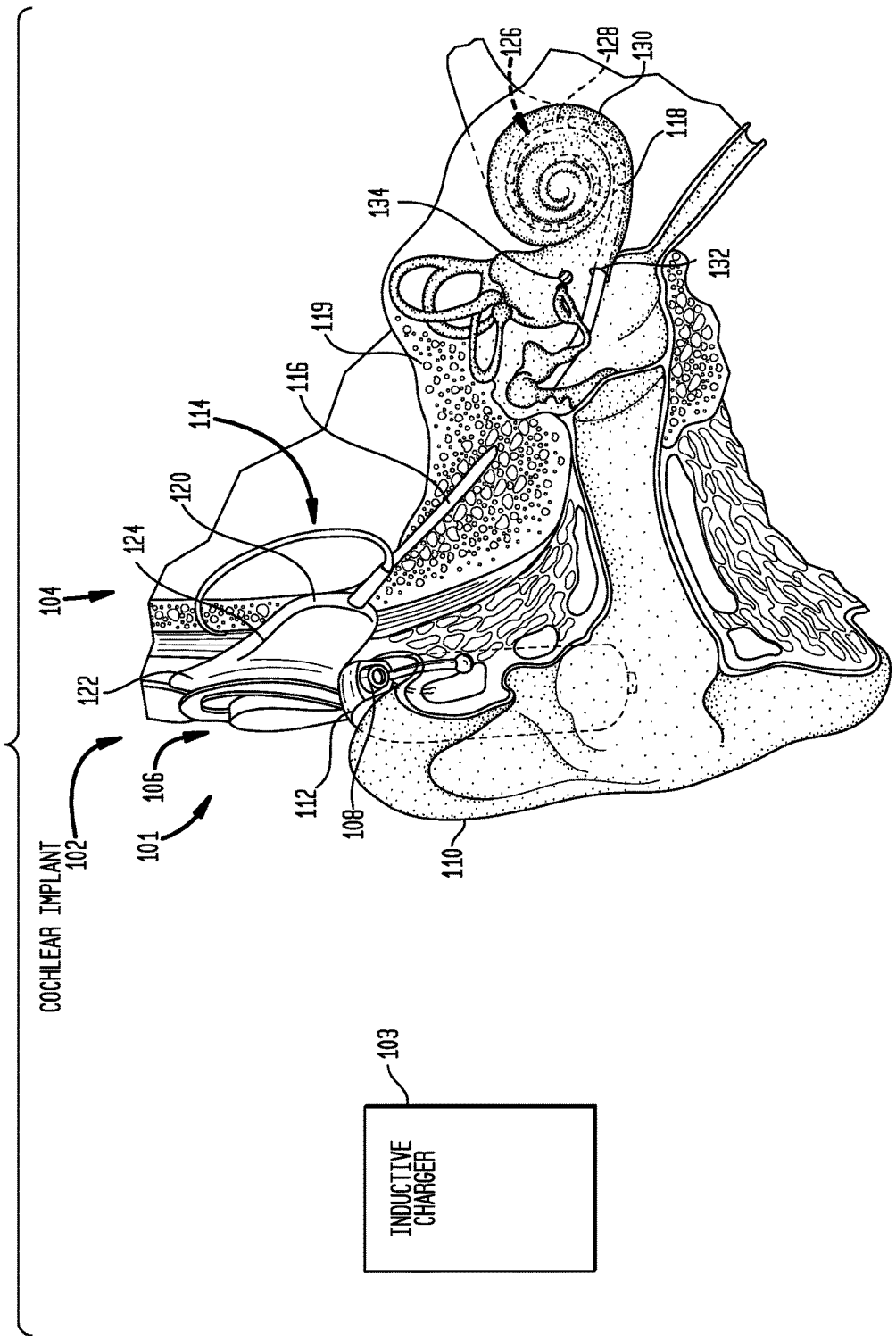
FIG. 1 is a schematic diagram illustrating a cochlear implant system in accordance with embodiments presented herein.

FIG. 1 is perspective view of an exemplary hearing system 100, namely a cochlear implant system, in which embodiments presented herein are implemented. The cochlear implant system 100 comprises a cochlear implant 102 and a charging component, sometimes referred to herein as an inductive charging station or inductive charger. Inductive charger 103 may have a number of different forms, such as a docking station, charging mat, etc.

The cochlear implant 102 includes an external component 101 and an internal or implantable component 104. The external component 101 is directly or indirectly attached to the body of the recipient and typically comprises an external radio frequency (RF) coil arrangement 106 and, generally, a magnet (not shown in FIG. 1) fixed relative to the external coil arrangement 106, one or more sound input elements 108 (e.g., microphones, telecoils, etc.) for detecting sound and a sound processing unit 112. The sound processing unit 112 includes at least one rechargeable battery, such as an integrated or removable lithium-ion (LiIon) battery, (not shown in FIG. 1) and a sound processor (also not shown in FIG. 1). The sound processor is configured to process electrical signals generated by a sound input element 108 that is positioned, in the depicted embodiment, by auricle 110 of the recipient. That is, the sound processor uses the signals received from the sound input element to generate data signals representative of received sounds. These data signals, as well as power signals, are transferred to the implantable component 104 via the external coil arrangement 106.

In the embodiment of FIG. 1, the sound processing unit 112 is a behind-the-ear sound processing unit that is electrically connected to the separate external coil arrangement 106 via a cable (not shown in FIG. 1). In certain embodiments, the sound processing unit may be a "button" or coil sound processing unit having, for example, a generally cylindrical shape. A coil sound processing unit is a component in which the sound processor, external coil arrangement, and external magnet are all disposed within (or adjacent to) the same housing configured to be worn at the same location as where an external coil is traditionally located.

The implantable component 104 comprises an implant body 114, a lead region 116, and an elongate intra-cochlear stimulating assembly 118. The implant body 114 comprises a stimulator unit 120, an internal RF coil arrangement 122, and an internal receiver/transceiver unit 124, sometimes referred to herein as transceiver unit 124. The transceiver unit 124 is connected to the internal coil arrangement 122 and, generally, a magnet (not shown) fixed relative to the internal coil arrangement 122.

The magnets in the external component 101 and implantable component 104 facilitate the operational alignment of the external coil arrangement 106 with the internal coil arrangement 122. The operational alignment of the coil arrangements enables the internal coil arrangement 122 to transmit/receive power and data to/from the external coil arrangement 106. More specifically, in certain examples, the external coil arrangement 106 transmits electrical signals (e.g., power and stimulation data signals) to the internal coil arrangement 122 via an RF link. Internal coil arrangement 122 typically includes a wire antenna coil that is electrical insulated by a flexible molding (e.g., silicone molding). In use, the transceiver unit 124 may be positioned in a recess of the temporal bone of the recipient and connected to the internal coil arrangement 122.

Elongate stimulating assembly 118 is configured to be at least partially implanted in cochlea 130 and includes a plurality of intra-cochlear stimulating contacts 128. The stimulating contacts 128 collectively form a contact array 126 and may comprise electrical contacts and/or optical contacts. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

As described further below, the inductive charger 103 is configured to inductively charge the rechargeable battery within the sound processing unit 112 via the external coil arrangement 106 (i.e., use an electromagnetic field to transfer energy from the inductive charger to the sound processing unit). That is, the coil arrangement, which is used to send power and/or data signals to the implantable component 104, is also used to receive power signals from the inductive charger 103 that are then used to charge the rechargeable battery. As such, the external coil arrangement 106 is sometimes referred to herein as a "dual-use" or "dual-function" coil arrangement.

Figure 2A:
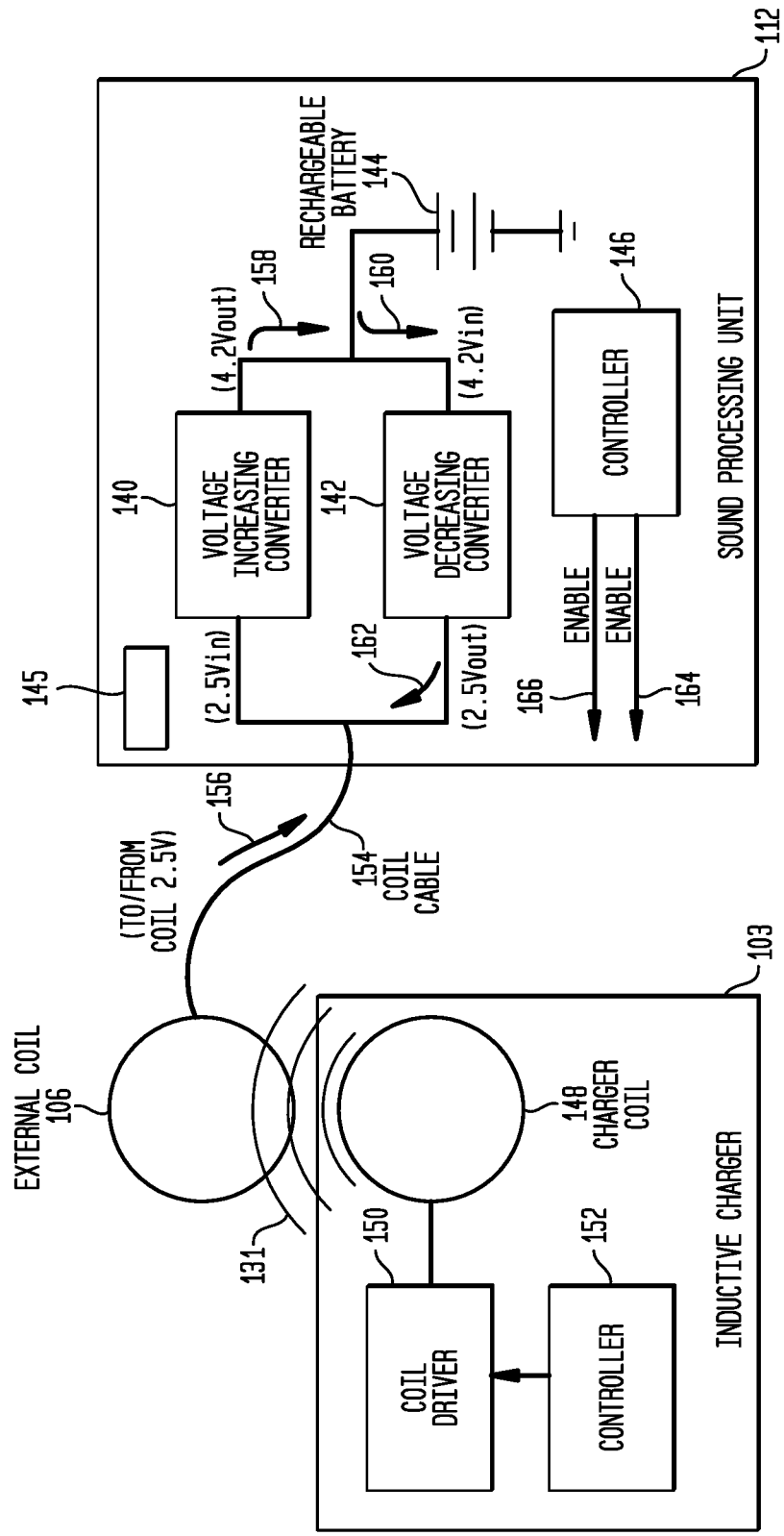
FIG. 2A is a block diagram illustrating one arrangement of the cochlear implant system of FIG. 1.

FIG. 2A is a simplified block diagram of the sound processing unit 112 and the inductive charger 103 of FIG. 1. For ease of illustration, only the components of sound processing unit 112 that relate to charging/power transfer are shown in FIG. 2A. As such, it is to be appreciated that the sound processing unit 112 may include other components that are not shown in FIG. 2A (e.g., sound input elements, a sound processor, data transceiver, etc.).

The sound processing unit 112 includes a voltage increasing converter 140, a voltage decreasing converter 142, at least one rechargeable battery 144, and a controller 146. The inductive charger 103 comprises a charger coil 148, a coil driver 150, and a controller 152.

In a first mode of operation of the sound processing unit 112, sometimes referred to herein as a "charging mode," the sound processing unit 112 is configured to receive power from the inductive charger 103 via an RF link formed between charger coil 148 and external coil arrangement 106. More specifically, when the external coil arrangement 106 is "docked" with inductive charger 103 (i.e., when the coil in the external coil arrangement 106 and the charger coil 148 are located proximate to one another and aligned to form an inductive coupling), controller 152 uses coil driver 150 and charger coil 148 to create a magnetic field. In one example, the charger coil 148 is a 5 Megahertz (MHz) coil that generates a 5 MHz magnetic field. The external coil arrangement 106 receives and rectifies the energy received from the magnetic field generated by the charger coil 148. The external coil arrangement 106 then passes the received energy to the sound processing unit 112 via the coil cable 154. As described further below, the power signals passed to the sound processing unit 112 are voltage-limited power signals (battery charging signals). The voltage-limited battery charging signals are represented in FIG. 2A by arrow 156. In a second mode of operation of the sound processing unit 112, sometimes referred to as herein as an "operational mode," the sound processing unit 112 is configured to send power and data signals to the implantable component 104 via an RF link formed between external coil arrangement 106 and the internal coil arrangement 122 (FIG. 1).

As noted above, FIG. 2A illustrates a dual-function coil arrangement in which external coil arrangement 106 is used both to (1) receive power from inductive charger 103, and for (2) transcutaneous communication (i.e., sending of power/data to the implantable component 104 (FIG. 1)). In general, the electronic components of sound processing unit 112 (e.g., transceiver) and/or of the external coil arrangement 106 (e.g., coil driver) that are used to send power/data to the implantable component 104 are designed to operate at voltages that are below the voltage of rechargeable battery 144. These electronic components are sometimes referred to herein as voltage-limited communication components. In one specific example, the rechargeable battery is a LiIon battery having a voltage of approximately 3.0 to approximately 4.2 V and the voltage-limited communication components operate at voltages below approximately 3.3 V and, in one example, below approximately 2.5 V.

Conventional battery charging techniques generally require the use of charging signals having high voltages that exceed the battery voltage and, as such, exceed the operating voltages of the voltage-limited communication components. As such, a potential problem with a dual-function external coil arrangement is that the voltage-limited communication components are susceptible to damage during receipt of battery charging signals. One solution is to add circuitry to the sound processing unit 112 that is configured to electrically disconnect/isolate the voltage-limited communication components while battery charging signals are received from the inductive charger 103 or to route the battery recharging signals around the voltage-limited communication components. However, these techniques typically require significant additional components, such as switches, that detrimentally affect the performance of the RF circuit. Another undesirable and costly solution is to design new communication components that operate at higher voltages (i.e., replace the voltage-limited communication components with components operating above the battery voltage).

FIG. 2A illustrates a solution in accordance with embodiments presented herein that enables continued use of the voltage-limited communication components (i.e., components generally having operating voltages below approximately 3 V and, in one example, below approximately 2.5 V) with a dual-function coil arrangement. More specifically, the techniques presented herein limit the voltage of the received battery charging signals 156 to a voltage level that is within the operating range of the voltage-limited communication components (e.g., limit the charging signals to a voltage of approximately 2.5 V to approximately 3.0 V to prevent damage to the voltage-limited components). This voltage limitation is, in general, contrary to conventional wireless charging techniques that operate using high-voltage charging signals in an effort to maximize power transfer and reduce charging times.

Since, as noted above, the voltage levels of the battery charging signals 156 are limited to a voltage level that does not damage the voltage-limited communication components, the battery charging signals inherently have a voltage level that is below the voltage level of the rechargeable battery 144. As such, the voltage-limited (low-voltage) battery charging signals 156 themselves are not useable for direct recharging of the battery 144. Therefore, in accordance with the first mode of operation of the embodiment illustrated in FIG. 2A, the voltage-limited battery charging signals 156 are sent to the voltage increasing converter 140. The voltage increasing converter 140, sometimes referred to herein as a step-up converter, is a direct current (DC)-DC power converter that is configured to generate an output voltage that is greater than its input voltage. In the example of FIG. 2A, the voltage increasing converter 140 takes the voltage-limited battery charging signals 156 and generates voltage-increased (high-voltage) battery charging signals (i.e., increases the voltage of the signals to be within a charging voltage range of the battery 144). The voltage-increased battery charging signals are represented in FIG. 2A by arrow 158. In general, the voltage-increased battery charging signals 158 have a voltage greater than the battery voltage. In one specific arrangement, the voltage-increased battery charging signals 158 have a voltage greater than 4.2 V.

The voltage increasing converter 140 is used to increase the received voltage to a level that is high enough to charge the battery 144. A control mechanism is needed to prevent the voltage increasing converter 140 from attempting to draw too much energy from the external coil arrangement 106 as such a circumstance could cause the voltage to drop off and cause the system to stop working. In one example, the control mechanism is a Maximum Power Point Tracking (MPPT) mechanism executed by the voltage increasing converter 140. The MPPT may be executed to decrease the output voltage if the input voltage of the voltage increasing converter 140 drops below a set voltage threshold. This feature is necessary in inductive charging because the power provided by the RF link is limited. This ensures that the maximum amount of power is transferred across the link and available to charge the battery.

Figure 2B:
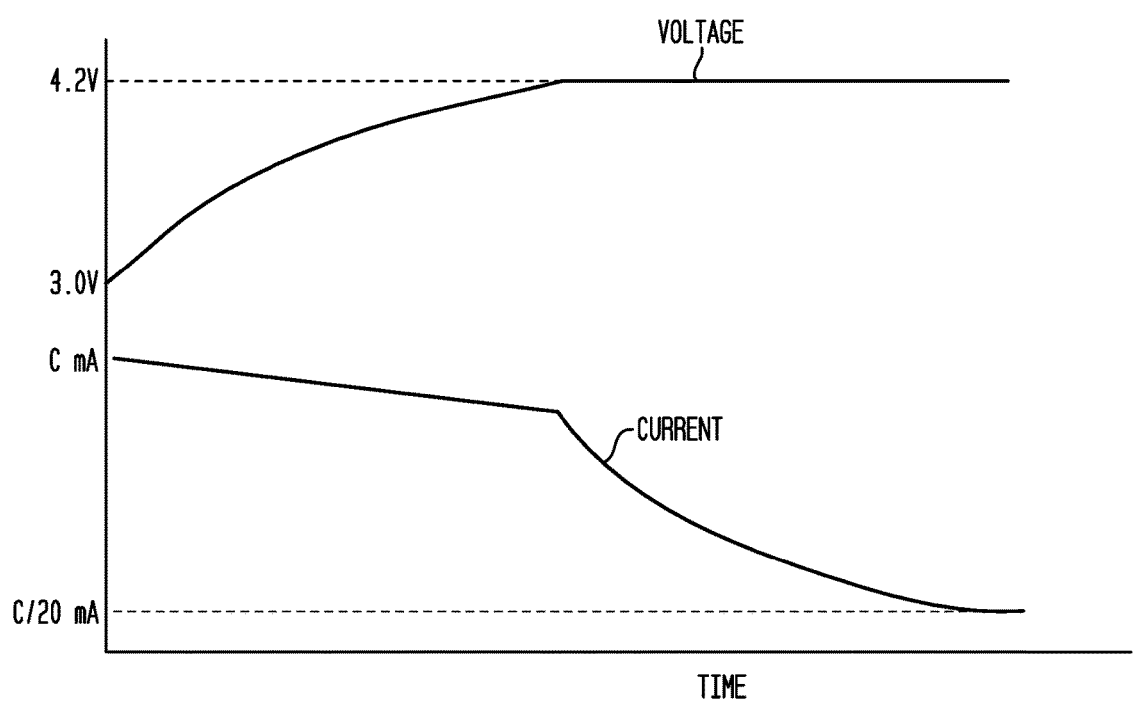
FIG. 2B is a plot of voltage and current curves for a battery charging method in accordance with embodiments presented herein.

The typical battery charging method for a LiIon battery involves a first phase of constant charge current and then a second phase of constant charge voltage, terminating when the charge current reaches a minimum value. In accordance with the embodiments presented herein, the voltage increasing converter 140 comprises, for example, a 4.2 V boost regulator, with the maximum power point tracking set to 2.0 V. The boost regulator supplies a constant 4.2 V, when required. The limiting of current required in the first phase of charging is implemented by limiting the power that can be transferred across the RF link. This method will result in longer charge times, but minimizes complexity in the sound processing unit 112. Since a constant power method is proposed, the charge current is not constant during the "constant current" phase, but rather will be higher when the battery voltage is close to discharged (3.0V) and will drop as the voltage rises towards 4.2V. This is illustrated in the plot of FIG. 2B.

As noted above, in the second mode of operation, the sound processing unit 112 uses the coil arrangement to transmit power/data to the implantable component 104. Power for use by the other components of the sound processor or for transmission to implantable component 104 is drawn from the rechargeable battery 144 at a high-voltage level (e.g., 4.2 V). The direct (high-voltage) battery signals are represented in FIG. 2A by arrow 160. However, the high voltage of the battery signals 160 is above the operating range of the voltage-limited communication components and, as such, can cause damage to those components. As such, during this second mode of operation, the battery voltage is reduced to a voltage-limited level by the voltage decreasing converter 142.

The voltage decreasing converter 142 is a voltage step down and current step up converter. In the example of FIG. 2A, the voltage decreasing converter 142 takes the direct (high-voltage) battery signals 160 and generates voltage-limited battery signals, represented in FIG. 2A by arrow 162. The voltage-limited battery signals 162 may then by used by components of the sound processing unit 112 or transmitted to implantable component 104 via the coil arrangement 106.

As noted above, the voltage increasing converter 140 and voltage decreasing converter 142 are used in the first and second modes of operation, respectively. The controller 146 in the sound processing unit 112 is configured to alternatively enable one of the voltage increasing converter 140 and the voltage decreasing converter 142. In other words, the controller 146 is configured to enable the voltage increasing converter 140 during the first mode of operation (i.e., when sound processing unit 112 receives power from the inductive charger 103). Since the voltage decreasing converter 142 is disabled during the first mode of operation, the voltage-limited charging signals 156 are passed to the voltage increasing converter 140. During the second mode of operation (i.e., when the sound processing unit 112 transmits power and/or data to the implantable component 104), the controller 146 is configured to enable the voltage decreasing converter 142 and the voltage increasing converter 140 is disabled. Since the voltage increasing converter 140 is disabled during the second mode of operation, the high-voltage battery signals 160 are passed to the voltage decreasing converter 142. FIG. 2A schematically illustrates a voltage increasing converter enable signal 164 and a voltage decreasing converter enable signal 166 that may be generated by the controller 146.

In certain embodiments, the voltage increasing converter 140 and voltage decreasing converter 142 each have their own inductor within the sound processing unit 112. In other embodiments, a single inductor in the sound processing unit 112 is shared by the voltage increasing converter 140 and voltage decreasing converter 142. In other embodiments, switched capacitor converters can be used that don't require an inductor. The voltage decreasing converter 142 could be replaced by a linear regulator (i.e., a Low DropOut regulator).

Figure 3:
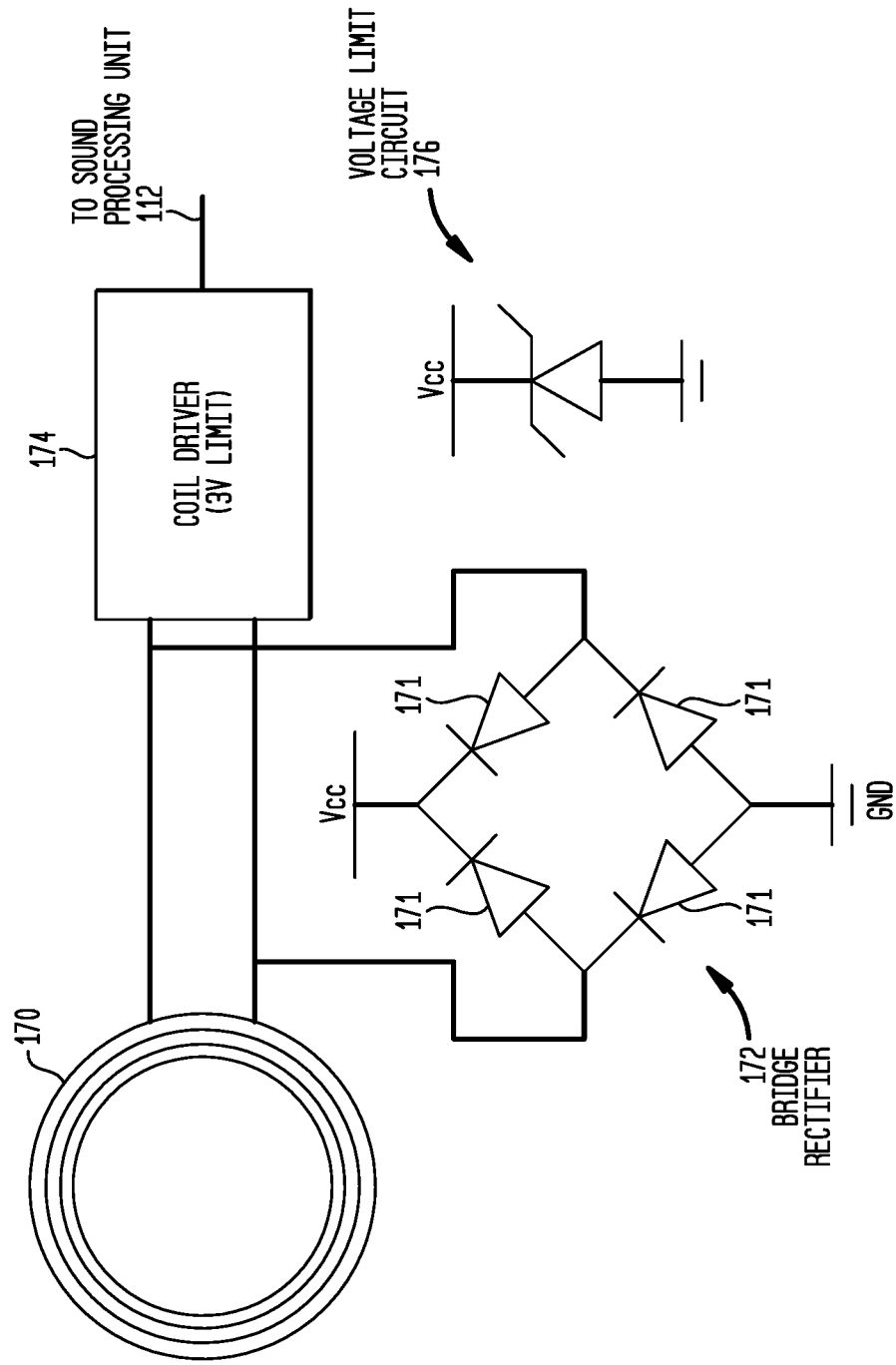
FIG. 3 is a schematic diagram of a dual-function coil arrangement in accordance with embodiments presented herein.

FIG. 3 is a schematic diagram illustrating one configuration for a dual-function coil arrangement, such as dual-function coil arrangement 106, in accordance with embodiments presented herein. As shown, dual-function coil arrangement 106 comprises an RF coil 170, a bridge rectifier 172, a coil driver 174, and a voltage limit circuit 176.

The RF coil 170 is a conductor, such as a wire, formed into a generally helical shape (i.e., a plurality of "turns"). The RF coil 170 is configured to receive the charging signals from the inductive charger 103 (FIG. 2A), transmit power/battery signals to the implantable component 104 (FIG. 1A), transmit data signals to the implantable component 104, and, in certain examples, receive data signals from the implantable component 104.

The signals received at the RF coil 170 are alternating current (AC) signals (e.g., 5 MHz AC signals). The bridge rectifier 172 is configured to convert the AC signals (e.g., 5 MHz AC signal) received by the RF coil 170 into a DC signal. The DC signal is provided to the coil driver 174 for forwarding to the sound processing unit 112 as the voltage-limited charging signals 156. In one specific example, the bridge rectifier 172 uses Schottky diodes added directly to the RF coil 170, which presents a voltage between Vcc and GND.

During sending of power and data to the implantable component, the diodes 171 in the bridge rectifier 172 do not enter forward bias and, as such, have no effect on the circuit. However, when receiving power from the inductive charger 103, Vcc is low and so the diodes 171 forward bias and charge up Vcc.

During battery charging, the voltage induced in the RF coil 170 depends upon the power sent by the inductive charger 103 and upon how much power is being drawn by the sound processing unit 112 to charge the rechargeable battery 144. If there is an imbalance (e.g., the inductive charger 103 sends more power than the battery 144 needs), then the induced voltage could rise above a safe operating level (i.e., the voltage could rise and potentially damage the coil driver and other components for used for communication with the implantable component 104). As such, in certain examples, there may be a need to limit the voltage at the input of the coil driver 174. In such examples, the dual-function coil arrangement 106 includes the voltage limit circuit 176 that is configured to dissipate unused power (i.e., power not passed through the coil driver to the sound processing unit 112). As such, the voltage limit circuit 176 operates to prevent damage to the electronics required for communication with the implant. The voltage limit circuit 176 may comprise, for example, a Zener diode. In other examples, the voltage limit circuit 176 may be one or more other components designed to limit the voltage or circuits made with multiple discrete components.

The voltage limit circuit 176 is shown in FIG. 3 as part of the coil arrangement 106. In other embodiments, the voltage limit circuit 176 may be part of the sound processing unit 112.

The voltage limit circuit 176 operates as a short-term technique to address an improper voltage increase at the dual-function coil arrangement 106. Embodiments of the present invention include other techniques that may be used to address an improper voltage increase at the dual-function coil arrangement 106.

For example, in one arrangement the sound processing unit 112 is configured to communicate with the inductive charger 103 to indicate, for example, when to reduce the transmitted charging power. More specifically, it is advantageous for the inductive charger 103 to initially send a high level of power to charge the battery 144, to send less power to the sound processing unit 112 when the battery 144 is nearing a fully charge state, and to send little or no power when the battery 144 is fully charged. As such, the sound processing unit 112 is configured to be able to send messages to the inductive charger 103 that may be used to adjust the power that is sent. In one example, a separate communication link may be used to send these messages to the inductive charger 103. However, a disadvantage of using a separate communication link is complexity in the design and the need to pair the inductive charger 103 and sound processing unit 112 before charging (e.g., a Bluetooth® communication channel requiring a pre-pairing process). Bluetooth® is a registered trademark owned by the Bluetooth® SIG.

In accordance with certain embodiments presented herein, instead of using a separate communication channel, the inductive charging link 131 that is used for sending the charging power from the inductive charger 103 to the sound processing unit 112 is also used to send information/messages from the sound processing unit to the inductive charger. Communication from the sound processing unit 112 to the inductive charger 103 over the inductive charging link 131 is sometimes referred to herein as "back-link communication."

In one example, the back-link communication (i.e., the communication from the sound processing unit 112 to the inductive charger) operates "on top of" (i.e., in a reverse direction to, and simultaneously with) the inductive charging link 131. More specifically, a load modulation technique (i.e., a load modulated back-link communication) is used by the sound processing unit 112 to communicate back to the inductive charger 103 while the inductive charger is sending power to the sound processing unit 112. When the inductive charger 103 sends power to the sound processing unit 112, the voltages in the circuit of the inductive charger are affected by the load presented at the external coil arrangement 106, as well as by the tuned frequency of the external coil arrangement. A change to the load on the external coil arrangement 106 or a change in the tuned frequency of the external coil arrangement 106 can be detected by the transmitter. As such, in one example the controller 152 of the inductive charger 103 is configured to monitor the peak voltage waveform across the charger coil 148.

Figure 4:
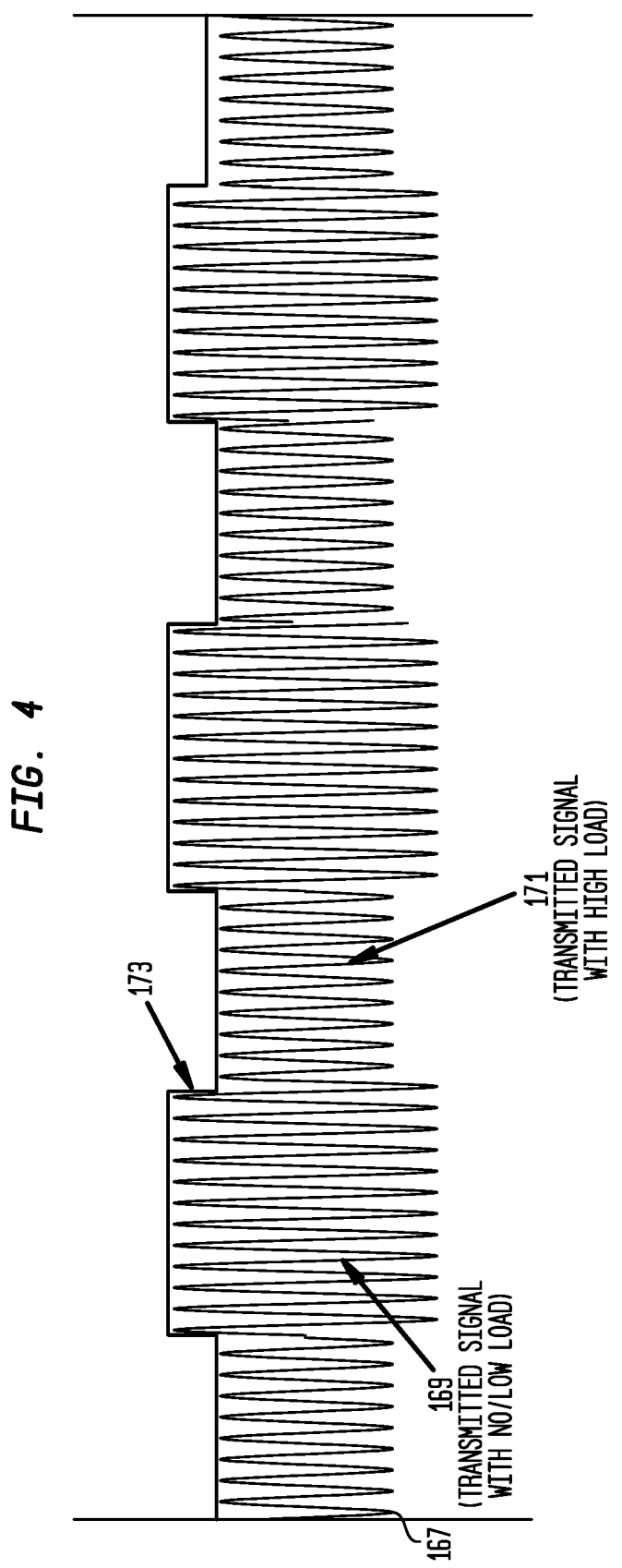
FIG. 4 is a plot illustrating the voltage across the coil of an inductive charger during load modulated back-link communication in accordance with embodiments presented herein.

FIG. 4 is a plot illustrating the voltage across the charger coil 148 of the inductive charger 103 during load modulated back-link communication in accordance with embodiments presented herein. More specifically, FIG. 4 first illustrates the transmitted signal 167 having portions 169 and 171. At portions 169, the signal is transmitted with little or no load at the external coil 106 (receiver), while at portions 171 the signal is transmitted with a high load at the external coil 106.

As shown in FIG. 4, the peak voltage of this waveform changes with changes to the load across the receive coil 106 (i.e., the transmitted signal is modulated by changing the load at the external coil). Therefore, the sound processing unit 112 can send information to the inductive charger 103 by changing the load across the coil 106. The sound processing unit 112 may include one or more components 145 configured to vary the load associated with/on the external coil arrangement 106 to communicate information to the inductive charger 103 over the inductive charging link 131. FIG. 4 illustrates the envelope 173 of the transmitted signal 167, where the envelope is used as the binary communication signal.

In another embodiment, rather than varying the load, the sound processing unit 112 is configured to inject energy into the receive coil 106 (i.e., receiving element injects power back towards the transmitter and on top of the transmitted power). The injected power may be detected at the inductive charger 103 through a voltage change at the charger coil 148. The transmit circuitry (not shown) of the sound processing unit 112 is used to push power over the top of the inductive charging link 131.

In a further embodiment, rather than varying the load, one or more other inductive charging link parameters may be adjusted by the components 145 for detection at the charger coil 148. For example, changes in the tuned frequency of the coil arrangement 106, the coupling coefficient of the inductive charging link 131, etc. can be initiated by components 145 and detected at the charger coil 148. In one specific example, the amount of energy received by the coil arrangement 106 can be reduced by adjusting the value of the tuning capacitor associated with the coil arrangement 106 or by shorting one or both ends of the coil to GND (i.e., detuning the coil arrangement 106).

In other examples, the inductive charging link 131 may be used for back-link communication by leaving regular gaps in the transmitted power. More specifically, the inductive charger 103 may be configured to regularly stop the transmission of power to the sound processing unit 112. Due to the regular nature of the gaps, the sound processing unit 112 may use these gaps in the power transmission to send signals across the inductive charging link 131. That is, the sound processing unit 112 uses the short gaps to transmit signals from the coil 106 to the charger coil 148 that can be detected at the controller 152 of the inductive charger 103 (i.e., a time interleaving scheme).

As detailed above, the back-link communication may take a number of different forms. Similarly, the type and/or content of the information/messages transmitted from the sound processing unit 112 to the inductive charger 103 over the inductive charging link 131 may also have a number of different forms/arrangements. In one example, the back-link communication uses a binary communication scheme in which a "low" load (i.e., a load detected at the charger coil 108 having a value below a first threshold) is considered a binary "zero" and a "high" load (i.e., a detected load above a second threshold) is considered a binary "one." Loads between the first and second thresholds may be ignored by the inductive charger 103 as reflecting the normal load for the inductive charging (i.e., the normal forward-link load).

The different low and high loads could be used by the sound processing unit 112 to send different messages to the inductive charger 103. In one form, the sound processing unit 112 uses the low and high loads to encode "start" and "stop" messages that cause the inductive charger to start and stop, respectively, the transmission of power to the sound processing unit. In a further embodiment, the sound processing unit 112 uses the low and high loads to encode a "near full charge" message indicating that the battery 144 is within a predetermined range of a full-charge. In response to receipt of the "near full charge" message, the inductive charger 103 reduces the amount of power sent to the sound processing unit 112. It is to be appreciated that the above specific messages are merely illustrative and that other messages are possible (e.g., messages made be encoded to cause the sending of a specific power level, sending an increased amount of power, initiate maintenance pulses, etc.).

As described above, the sound processing unit 112 has a configuration that enables the use of a dual-function coil arrangement 106 (i.e., the same coil for battery charging and transcutaneous communication). However, it is contemplated that the inductive charger 103 could potentially come into contact with older/conventional sound processing units that are not properly configured to receive inductive charging signals. This is a special problem arising from the fact that the conventional sound processing units may use a coil of a similar size and shape as the dual-function coil arrangement, yet will respond differently when brought near an inductive charger (i.e., conventional sound processing unit could be damaged while the batteries of sound processing units in accordance with embodiments presented herein are charged). As such, inductive chargers in accordance with embodiments present herein, such as inductive charger 103, may be configured with features to prevent damage to conventional sound processing units.

More specifically, in one embodiment, inductive charger 103 has a standby mode of operation in which probing signals that are large enough to be detected by sound processing units, but which are configured so as not to damage conventional sound processing units, (e.g., short bursts of power) are periodically transmitted via the charger coil 148. These probing signals may be used to detect when a sound processing unit with a dual-coil arrangement is present and ready for charging.

Similarly, a sound processing unit with a dual-coil arrangement, such as sound processing unit 112, can monitor the voltage at the external coil 106 to detect the probing signals. Sound processing unit 112 may respond to the probing signals with a message that initiates the transmission of charging signals. In one example, the inductive charger 103 can be detected by a method where the coil supply line is momentarily disconnected from the sound processing unit 112 before measuring the coil voltage and the presence of the inductive charger 103 is determined from the rate at which the coil voltage decays.

Additionally, the inductive charger 103 could detect the presence of a sound processing unit with a dual-coil arrangement through changes in the probing signals (e.g., through load modulation affect, the voltage detected at the charger coil 148 could change in a predetermined manner when a sound processing unit with a dual-coil arrangement is present).

In one example, control of the charging process is handled by the controller (processor) 146 inside the sound processing unit 112. If the sound processing unit 112 has been turned off and is placed in proximity to the inductive charger 103, the controller 146 is configured to turn on to allow charging (e.g., turns on in response to detection of the probing signals). Similarly, once the battery 114 has been charged, the controller 146 may be configured to turn itself off to preserve the charge in the battery and may be configured to remain off while located in proximity to inductive charger 103. The controller 146 may be configured to activate when it detects that the sound processing unit 112 is no longer in proximity to the inductive charger (e.g., when the absence of probing signals is detected).

Figure 5:
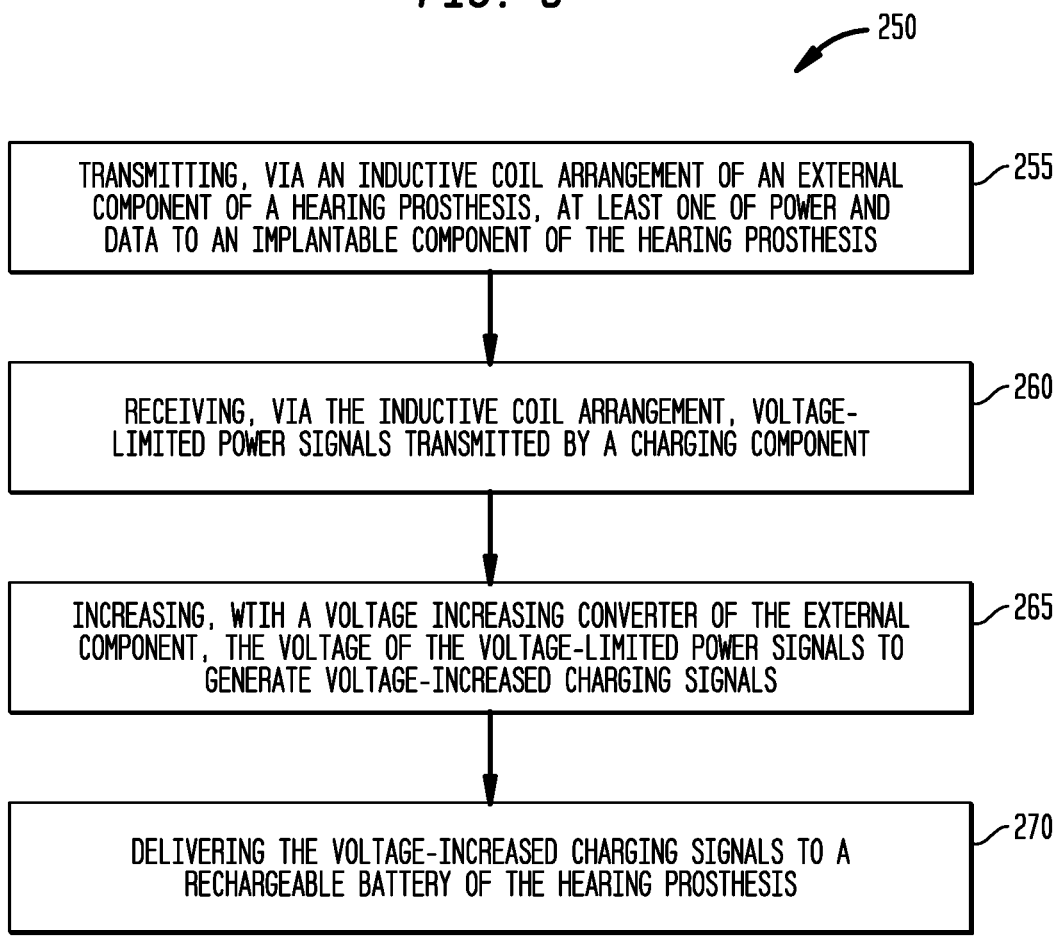
FIG. 5 is a flowchart of a method in accordance with embodiments presented herein.

FIG. 5 is a flowchart of a method 250 in accordance with embodiments presented herein. Method 250 begins at 255 where an inductive coil arrangement of an external component of a hearing prosthesis transmits at least one of power and data to an implantable component of the hearing prosthesis. At 260, the inductive coil arrangement receives voltage-limited power signals transmitted by a charging component. At 265, a voltage increasing converter of the external component increases the voltage of the voltage-limited power signals to generate voltage-increased charging signals. At 270, the voltage-increased charging signals are delivered to a rechargeable battery of the hearing prosthesis.

In summary, presented herein are inductive charging techniques in which power signals are received at a voltage that is below the battery voltage, thereby preventing damage to other components of the receiving device. A step-up circuit is then used to increase the voltage of the power signals to a level that is need to charge the battery.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device system, comprising:
an inductive charger including a charger coil;
an external component including:
  a rechargeable battery,
  an inductive coil arrangement configured to form an inductive charging link with the charger coil to receive power signals from the inductive charger,
  a voltage increasing converter configured to step-up a voltage of the power signals received from the inductive charger for use in charging the rechargeable battery, and
  a voltage decreasing converter configured to step-down a voltage of signals obtained from the rechargeable battery; and
an implantable component including an implantable coil, wherein the inductive coil arrangement is further configured to form a transcutaneous link with the implantable coil to transmit at least one of data and power to the implantable component.

2. The implantable medical device system of claim 1, wherein the voltage increasing converter and voltage decreasing converter are connected in parallel between the inductive coil and the rechargeable battery, and further comprising:
a controller configured to enable the voltage decreasing converter or the voltage increasing converter.

3. The implantable medical device system of claim 1, further comprising:
a voltage limit circuit.

4. The implantable medical device system of claim 1, wherein the voltage increasing converter is configured to execute Maximum Power Point Tracking (MPPT) to decrease an output voltage of the voltage increasing converter if an input voltage of the voltage increasing converter drops below a voltage threshold.

5. The implantable medical device system of claim 1, wherein the external component includes one or more components configured to:
vary a load associated with the inductive coil arrangement to communicate information to the inductive charger over the inductive charging link.

6. The implantable medical device system of claim 1, wherein the external component includes one or more components configured to:
vary a tuned frequency of the inductive coil arrangement to communicate information to the inductive charger over the inductive charging link.

7. The implantable medical device system of claim 1, wherein the external component includes one or more components configured to:
inject power onto the inductive charging link to communication information to the inductive charger.

8. An implantable medical device system, comprising:
an inductive charger including a charger coil;
an external component, comprising:
  a rechargeable battery;
  a dual-function coil arrangement configured for transcutaneous communication with an implantable component of the implantable medical device system, wherein the dual-function coil arrangement is further configured to receive voltage-limited charging signals from the inductive charger; and
  a voltage increasing converter and a voltage decreasing converter connected in parallel between the dual-function coil arrangement and the rechargeable battery.

9. The implantable medical device system of claim 8, wherein the voltage increasing converter is configured to step-up a voltage of the voltage-limited charging signals received at the dual-function coil arrangement for use in charging the rechargeable battery.

10. The implantable medical device system of claim 8, wherein the voltage decreasing converter is configured to step-down a voltage of signals obtained from the rechargeable battery.

11. The implantable medical device system of claim 8, wherein the external component further comprises a controller configured to enable the voltage decreasing converter or the voltage increasing converter.

12. The implantable medical device system of claim 8, wherein the voltage increasing converter is configured to execute Maximum Power Point Tracking (MPPT) to decrease an output voltage of the voltage increasing converter if an input voltage of the voltage increasing converter drops below a voltage threshold.

13. The implantable medical device system of claim 8, wherein the external component further comprises one or more components configured to vary a load associated with the inductive coil arrangement to communicate information to the inductive charger over the inductive charging link.

14. The implantable medical device system of claim 8, wherein the external component further comprises one or more components configured to vary a tuned frequency of the inductive coil arrangement to communicate information to the inductive charger over the inductive charging link.

15. The implantable medical device system of claim 8, wherein the external component further comprises one or more components configured to inject power onto the inductive charging link to communicate information to the inductive charger.

16. A method, comprising:
transmitting, via an external coil arrangement of an external component of a hearing prosthesis, at least one of power and data to an implantable component of the hearing prosthesis, wherein the implantable component includes an implantable coil, wherein the external coil arrangement is further configured to form a transcutaneous link with the implantable coil to transmit the at least one of data and power to the implantable component;
receiving, via the external coil arrangement, voltage-limited power signals transmitted by a charger coil of an inductive charger over an inductive charging link;
increasing, with a voltage increasing converter of the external component, the voltage of the voltage-limited power signals to generate voltage-increased charging signals;
delivering the voltage-increased charging signals to a rechargeable battery of the hearing prosthesis;
obtaining signals from the rechargeable battery; and
decreasing, with a voltage decreasing converter, a voltage of the signals obtained from the rechargeable battery.

17. The method of claim 16, further comprising:
receiving, via the external coil arrangement, low-power probing signals transmitted by the charging component.

18. The method of claim 16, further comprising:
varying a load associated with the external coil arrangement to communicate information to the charging component over the inductive charging link.

19. The method of claim 16, further comprising:
varying a tuned frequency of the external coil arrangement to communicate information to the charging component over the inductive charging link.

20. The method of claim 16, further comprising:
injecting power onto the inductive charging link to communicate information to the charging component.

* * * * *